United States Patent
Debaud et al.

(10) Patent No.: US 9,918,925 B2
(45) Date of Patent: *Mar. 20, 2018

(54) COMPOSITION COMPRISING POLYMER PARTICLES, ALKYLCELLULOSE PARTICLES AND WATER

(71) Applicant: L'ORÉAL, Paris (FR)

(72) Inventors: Roshanak Debaud, L'haÿ les Roses (FR); Sylvie Manet, Verrieres le Buisson (FR)

(73) Assignee: L'ORÉAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/974,531

(22) Filed: Dec. 18, 2015

(65) Prior Publication Data

US 2016/0184211 A1    Jun. 30, 2016

Related U.S. Application Data

(60) Provisional application No. 62/093,802, filed on Dec. 18, 2014.

(51) Int. Cl.

| A61K 8/81 | (2006.01) |
|---|---|
| A61K 8/41 | (2006.01) |
| A61Q 1/06 | (2006.01) |
| A61K 8/73 | (2006.01) |
| A61K 8/31 | (2006.01) |
| A61K 8/02 | (2006.01) |

(52) U.S. Cl.
CPC .......... *A61K 8/8152* (2013.01); *A61K 8/0241* (2013.01); *A61K 8/31* (2013.01); *A61K 8/731* (2013.01); *A61Q 1/06* (2013.01); *A61K 2800/412* (2013.01); *A61K 2800/52* (2013.01); *A61K 2800/614* (2013.01)

(58) Field of Classification Search
None
See application file for complete search history.

(56) References Cited

U.S. PATENT DOCUMENTS

| 5,389,363 | A | * | 2/1995 | Snyder ............... A61K 8/585 |
|---|---|---|---|---|
| | | | | 424/401 |
| 5,616,598 | A | | 4/1997 | Lion et al. |
| 5,851,517 | A | | 12/1998 | Mougin et al. |
| 5,945,095 | A | | 8/1999 | Mougin et al. |
| 2004/0137028 | A1 | | 7/2004 | de la Poterie |
| 2011/0243864 | A1 | | 10/2011 | Farcet et al. |

FOREIGN PATENT DOCUMENTS

| EP | 0 749 746 | 12/1996 |
|---|---|---|
| EP | 0 749 747 | 12/1996 |
| FR | 2 785 530 | 5/2000 |
| FR | 2 937 645 | 4/2010 |
| FR | 2 972 630 | 9/2012 |
| FR | 2 972 631 | 9/2012 |

OTHER PUBLICATIONS

U.S. Appl. No. 14/575,259, filed Dec. 18, 2014, 2016/0175204, Rita Jaky El-Khouri.
U.S. Appl. No. 14/575,419, filed Dec. 18, 2014, 2016/0175230, Susan Halpern-Chirch.
U.S. Appl. No. 14/575,636, filed Dec. 18, 2014, US2016/0175231, Susan Halpern-Chirch.
U.S. Appl. No. 14/575,866, filed Dec. 18, 2014. US2016/0175232, Rita Jaky El-Khouri.
U.S. Appl. No. 14/974,531, filed Dec. 18, 2015, 2016/0184211, Roshanak Debaud.
U.S. Appl. No. 14/974,706, filed Dec. 18, 2015, 2016/0175205, Roshanak Debaud.
U.S. Appl. No. 15/105,293, filed Dec. 16, 2016, 2016/0317423, Julien Portal.
U.S. Appl. No. 15/533,444, filed Jun. 6, 2017, Hong Li.
U.S. Appl. No. 15/534,216, filed Jun. 8, 2017, Roshanak Debaud.
U.S. Appl. No. 15/537,082, filed Jun. 16, 2017, Laure Daubersies.
U.S. Appl. No. 15/537,422, Philippe Ilekti.
U.S. Appl. No. 15/537,423, Philippe Ilekti.

* cited by examiner

*Primary Examiner* — Kyle Purdy
(74) *Attorney, Agent, or Firm* — Oblon, McClelland, Maier & Neustadt, L.L.P.

(57) ABSTRACT

The present invention relates to a composition comprising particles of at least one polymer that is surface-stabilized with a stabilizer, the polymer of the particles being a $C_1$-$C_4$ alkyl (meth)acrylate polymer; the stabilizer being an isobornyl (meth)acrylate polymer chosen from isobornyl (meth)acrylate homopolymer and statistical copolymers of isobornyl (meth)acrylate and of $C_1$-$C_4$ alkyl (meth)acrylate present in an isobornyl (meth)acrylate/$C_1$-$C_4$ alkyl (meth)acrylate weight ratio of greater than 4; at least one hydrocarbon-based oil, at least alkyl cellulose, the alkyl residue of which comprises between 2 and 6 carbon atoms; and water.

The invention also relates to a process for making up and/or caring for human keratin materials, in which the composition according to any one of the preceding claims is applied.

24 Claims, No Drawings

COMPOSITION COMPRISING POLYMER PARTICLES, ALKYLCELLULOSE PARTICLES AND WATER

CROSS-REFERENCE TO RELATED APPLICATIONS

This application claims the benefit of priority of U.S. Provisional Application No. 62/093,802, filed Dec. 18, 2014, the entire content of which is incorporated herein by reference.

The present invention relates to compositions for making up and/or caring for human keratin materials, such as the lips.

These compositions are well known and although they have specific properties depending on their use, there has been a very clear trend for a few years toward developing compositions with improved persistence. This avoids, on the one hand, the need to reapply the composition too often and, on the other hand, reduces transfer onto supports with which the made-up areas may come into contact (clothing, cups, etc.) or else their removal via the action of external agents (sebum, food, rain, etc.).

It is for this reason that the compositions for which this property is sought generally comprise at least one film-forming agent. The latter is often a polymer in a solubilized form or dispersed in one of the phases of the composition. It allows the composition, once applied, to form after drying a film that is more cohesive and persistent on the support.

One of the problems encountered with such film-forming agents is the fact that the resulting compositions give a deposit which may be considered too tacky, often giving rise to difficulties in applying the composition.

Cosmetic compositions are thus sought, for example intended for making up and/or caring for keratin materials, such as the lips, which comprise at least one film-forming agent and which make it possible to deposit a comfortable, non-tacky film which has good persistence and in particular good resistance to oils.

One subject of the invention is thus a composition comprising particles of at least one polymer that is surface-stabilized with a stabilizer, the polymer of the particles being a $C_1$-$C_4$ alkyl (meth)acrylate polymer; the stabilizer being an isobornyl (meth)acrylate polymer chosen from isobornyl (meth)acrylate homopolymer and statistical copolymers of isobornyl (meth)acrylate and of $C_1$-$C_4$ alkyl (meth)acrylate present in an isobornyl (meth)acrylate/$C_1$-$C_4$ alkyl (meth)acrylate weight ratio of greater than 4; at least one hydrocarbon-based oil, at least alkyl cellulose, the alkyl residue of which comprises between 2 and 6 carbon atoms; water.

A subject of the invention is also a process for making up and/or caring for keratin materials, in particular the lips, which consists in applying said composition.

However, other advantages will emerge more clearly on reading the description and the examples that follow.

It should be noted that, in the remainder of the description, unless otherwise indicated, the limits indicated for a range are included in that range.

The expressions "at least one" and "several" are used without distinction.

Hydrocarbon-Based Oil

The composition according to the invention comprises a first hydrocarbon-based oil.

This oil may be volatile (saturating vapour pressure greater than or equal to 0.13 Pa measured at 25° C.) or non-volatile (saturating vapour pressure less than 0.13 Pa measured at 25° C.).

Preferably, the hydrocarbon-based oil is volatile.

The hydrocarbon-based oil is an oil (non-aqueous compound) that is liquid at room temperature (25° C.).

The term "hydrocarbon-based oil" means an oil formed essentially from, or even consisting of, carbon and hydrogen atoms, and optionally oxygen and nitrogen atoms, and not containing any silicon or fluorine atoms. It may contain alcohol, ester, ether, carboxylic acid, amine and/or amide groups.

The hydrocarbon-based oil may be chosen from:
hydrocarbon-based oils containing from 8 to 16 carbon atoms, and especially:
  branched $C_8$-$C_{16}$ alkanes, for instance $C_8$-$C_{16}$ isoalkanes of petroleum origin (also known as isoparaffins), for instance isododecane (also known as 2,2,4,4,6-pentamethylheptane), isodecane, isohexadecane and, for example, the oils sold under the trade name Isopar or Permethyl,
  linear alkanes, for instance n-dodecane ($C_{12}$) and n-tetradecane ($C_{14}$) sold by Sasol under the respective references Parafol 12-97 and Parafol 14-97, and also mixtures thereof, the undecane-tridecane mixture, the mixtures of n-undecane ($C_{11}$) and of n-tridecane ($C_{13}$) obtained in Examples 1 and 2 of patent application WO 2008/155 059 from the company Cognis, and mixtures thereof,
short-chain esters (containing from 3 to 8 carbon atoms in total) such as ethyl acetate, methyl acetate, propyl acetate or n-butyl acetate,
hydrocarbon-based oils of plant origin such as triglycerides consisting of fatty acid esters of glycerol, the fatty acids of which may have chain lengths varying from $C_4$ to $C_{24}$, these chains possibly being linear or branched, and saturated or unsaturated; these oils are especially heptanoic or octanoic acid triglycerides, or alternatively wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion-flower oil and musk rose oil; shea butter; or else caprylic/capric acid triglycerides, for instance those sold by the company Stéarineries Dubois or those sold under the names Miglyol 810®, 812® and 818® by the company Dynamit Nobel,
synthetic ethers containing from 10 to 40 carbon atoms,
linear or branched hydrocarbons of mineral or synthetic origin, such as petroleum jelly, polydecenes, hydrogenated polyisobutene such as Parleam®, squalane and liquid paraffins, and mixtures thereof,
synthetic esters such as oils of formula $R_1COOR_2$ in which $R_1$ represents a linear or branched fatty acid residue containing from 1 to 40 carbon atoms and $R_2$ represents an in particular branched hydrocarbon-based chain containing from 1 to 40 carbon atoms, on the condition that $R_1+R_2 \geq 10$, for instance purcellin oil (cetostearyl octanoate), isopropyl myristate, isopropyl palmitate, $C_{12}$ to $C_{15}$ alkyl benzoates, hexyl laurate, diisopropyl adipate, isononyl isononanoate, 2-ethylhexyl palmitate, isostearyl isostearate, 2-hexyldecyl laurate, 2-octyldecyl palmitate, 2-octyldodecyl myristate, alkyl or polyalkyl heptanoates, octanoates, decanoates or ricinoleates such as propylene glycol dioctanoate; hydroxylated esters such as isostearyl lactate, diisostearyl malate and 2-octyldodecyl lactate; polyol esters and pentaerythritol esters, fatty alcohols that are liquid at room temperature, with a branched and/or unsaturated carbon-based chain containing from 12 to 26 carbon atoms, for instance octyldodecanol, isostearyl alcohol, oleyl alcohol, 2-hexyldecanol, 2-butyloctanol and 2-undecylpentadecanol, a mixture thereof.

More particularly, the content of hydrocarbon-based oil(s) ranges from 20% to 75% by weight and preferably from 20% to 60% by weight, even more preferably from 20% to 50% by weight relative to the weight of the composition.

This hydrocarbon-based oil may be provided totally or partly with the surface-stabilized polymer particles, in particular when these particles are introduced into the composition in the form of a pre-prepared dispersion of surface-stabilized polymer particles. In this case, the hydrocarbon-based oil present in the composition represents at least the non-aqueous medium of the dispersion of polymer particles.

Advantageously, the hydrocarbon-based oil is apolar (thus formed solely from carbon and hydrogen atoms).

The hydrocarbon-based oil is preferably chosen from hydrocarbon-based oils containing from 8 to 16 carbon atoms and better still from 12 to 16 carbon atoms, in particular the apolar oils described previously.

Preferentially, the hydrocarbon-based oil is isododecane. More particularly, the isododecane content ranges from 20% to 75% by weight and preferably from 20% to 60% by weight, even more preferably from 20% to 50% by weight relative to the weight of the composition.

Preferably, the hydrocarbon-based oil(s), in particular isododecane, constitute the only oil(s) in the composition, or is (are) present in a predominant weight content relative to the additional oil(s) that may be present in the composition.

In accordance with a particular embodiment of the invention, if the composition contains one or more nonvolatile oils, the content thereof advantageously does not exceed 15% by weight, more particularly does not exceed 10% by weight, preferably 5% by weight relative to the weight of the composition, better still less than 2% by weight relative to the weight of the composition, or even does not contain any nonvolatile oil(s).

Polymer Particles

The composition according to the invention moreover comprises particles, which are generally spherical, of at least one surface-stabilized polymer.

Preferably, the particles are introduced into the composition in the form of a dispersion of particles, which are generally spherical, of at least one surface-stabilized polymer, in an oily medium, advantageously containing at least a hydrocarbon-based oil, as defined previously.

The polymer of the particles is a $C_1$-$C_4$ alkyl (meth)acrylate polymer.

The $C_1$-$C_4$ alkyl (meth)acrylate monomers may be chosen from methyl (meth)acrylate, ethyl (meth)acrylate, n-propyl (meth)acrylate, isopropyl (meth)acrylate, n-butyl (meth)acrylate and tert-butyl (meth)acrylate.

A $C_1$-$C_4$ alkyl acrylate monomer is advantageously used. Preferentially, the polymer of the particles is a methyl acrylate and/or ethyl acrylate polymer.

The polymer of the particles may also comprise an ethylenically unsaturated acid monomer or the anhydride thereof, chosen especially from ethylenically unsaturated acid monomers comprising at least one carboxylic, phosphoric or sulfonic acid function, such as crotonic acid, itaconic acid, fumaric acid, maleic acid, maleic anhydride, styrenesulfonic acid, vinylbenzoic acid, vinylphosphoric acid, acrylic acid, methacrylic acid, acrylamidopropanesulfonic acid or acrylamidoglycolic acid, and salts thereof.

Preferably, the ethylenically unsaturated acid monomer is chosen from (meth)acrylic acid, maleic acid and maleic anhydride.

The salts may be chosen from salts of alkali metals, for example sodium or potassium; salts of alkaline-earth metals, for example calcium, magnesium or strontium; metal salts, for example zinc, aluminium, manganese or copper; ammonium salts of formula $NH_4^+$; quaternary ammonium salts; salts of organic amines, for instance salts of methylamine, dimethylamine, trimethylamine, triethylamine, ethylamine, 2-hydroxyethylamine, bis(2-hydroxyethyl)amine or tris(2-hydroxyethyl)amine; lysine or arginine salts.

The polymer of the particles may thus comprise or consist essentially of 80% to 100% by weight of $C_1$-$C_4$ alkyl (meth)acrylate and of 0 to 20% by weight of ethylenically unsaturated acid monomer, relative to the total weight of the polymer.

According to a first embodiment of the invention, the polymer consists essentially of a polymer of one or more $C_1$-$C_4$ alkyl (meth)acrylate monomers.

According to a second embodiment of the invention, the polymer consists essentially of a copolymer of $C_1$-$C_4$ (meth)acrylate and of (meth)acrylic acid or maleic anhydride.

The polymer of the particles may be chosen from:
methyl acrylate homopolymers
ethyl acrylate homopolymers
methyl acrylate/ethyl acrylate copolymers
methyl acrylate/ethyl acrylate/acrylic acid copolymers
methyl acrylate/ethyl acrylate/maleic anhydride copolymers
methyl acrylate/acrylic acid copolymers
ethyl acrylate/acrylic acid copolymers
methyl acrylate/maleic anhydride copolymers
ethyl acrylate/maleic anhydride copolymers.

Advantageously, the polymer of the particles is a non-crosslinked polymer.

The polymer of the particles preferably has a number-average molecular weight ranging from 2000 to 10 000 000 and preferably ranging from 150 000 to 500 000.

In the case of a particle dispersion, the polymer of the particles may be present in the dispersion in a content ranging from 21% to 58.5% by weight and preferably ranging from 36% to 42% by weight, relative to the total weight of the dispersion.

The stabilizer is an isobornyl (meth)acrylate polymer chosen from isobornyl (meth)acrylate homopolymer and statistical copolymers of isobornyl (meth)acrylate and of $C_1$-$C_4$ alkyl (meth)acrylate present in an isobornyl (meth)acrylate/$C_1$-$C_4$ alkyl (meth)acrylate weight ratio of greater than 4, preferably greater than 4.5 and even more advantageously greater than or equal to 5. Advantageously, said weight ratio ranges from 4.5 to 19, preferably from 5 to 19 and more particularly from 5 to 12.

Advantageously, the stabilizer is chosen from:
isobornyl acrylate homopolymers
statistical copolymers of isobornyl acrylate/methyl acrylate
statistical copolymers of isobornyl acrylate/methyl acrylate/ethyl acrylate
statistical copolymers of isobornyl methacrylate/methyl acrylate
in the weight ratio described previously.

Preferably, the stabilizer is soluble in the hydrocarbon-based oil(s), in particular soluble in isododecane.

The stabilizing polymer preferably has a number-average molecular weight ranging from 10 000 to 400 000 and preferably ranging from 20 000 to 200 000.

The stabilizer is in contact with the surface, in particular of the polymer particles, and thus makes it possible to stabilize these particles at the surface, in order to keep these particles in dispersion in the non-aqueous medium of the dispersion.

According to a theory which should not limit the scope of the present invention, the inventors put forward the hypothesis that the surface stabilization of the $C_1$-$C_4$ alkyl (meth)acrylate polymer particles results from a phenomenon of surface adsorption of the stabilizer onto the $C_1$-$C_4$ alkyl (meth)acrylate polymer particles.

Advantageously, the combination of the stabilizer+polymer of the particles, present in particular in the dispersion comprises from 10% to 50% by weight of polymerized isobornyl (meth)acrylate and from 50% to 90% by weight of polymerized $C_1$-$C_4$ alkyl (meth)acrylate, relative to the total weight of the combination of the stabilizer+polymer of the particles.

Preferentially, the combination of the stabilizer+polymer of the particles present in particular in the dispersion comprises from 15% to 30% by weight of polymerized isobornyl (meth)acrylate and from 70% to 85% by weight of polymerized $C_1$-$C_4$ alkyl (meth)acrylate, relative to the total weight of the combination of the stabilizer+polymer of the particles.

When the polymer particles are provided in the composition in the form of a pre-prepared dispersion, the oily medium of this polymer dispersion comprises a first hydrocarbon-based oil. Reference may be made to that which has been indicated previously concerning this oil as regards its nature.

Advantageously, the hydrocarbon-based oil is apolar and preferably chosen from hydrocarbon-based oils containing from 8 to 16 carbon atoms, in particular the apolar oils described previously.

Preferentially, the hydrocarbon-based oil is isododecane.

The polymer particles, in particular in the dispersion, preferably have an average size, especially a number-average size, ranging from 50 to 500 nm, especially ranging from 75 to 400 nm and better still ranging from 100 to 250 nm.

In general, a dispersion of surface-stabilized polymer particles that is suitable for use in the invention may be prepared in the following manner, which is given as an example.

The polymerization may be performed in dispersion, i.e. by precipitation of the polymer during formation, with protection of the formed particles with a stabilizer.

In a first step, the stabilizing polymer is prepared by mixing the constituent monomer(s) of the stabilizing polymer, with a radical initiator, in a solvent known as the synthesis solvent, and by polymerizing these monomers. In a second step, the constituent monomer(s) of the polymer of the particles are added to the stabilizing polymer formed and polymerization of these added monomers is performed in the presence of the radical initiator.

When the non-aqueous medium is a non-volatile hydrocarbon-based oil, the polymerization may be performed in an apolar organic solvent (synthesis solvent), followed by adding the non-volatile hydrocarbon-based oil (which should be miscible with said synthesis solvent) and selectively distilling off the synthesis solvent.

A synthesis solvent which is such that the monomers of the stabilizing polymer and the free-radical initiator are soluble therein, and the polymer particles obtained are insoluble therein, so that they precipitate therein during their formation, is thus chosen.

In particular, the synthesis solvent may be chosen from alkanes such as heptane or cyclohexane.

When the non-aqueous medium is a volatile hydrocarbon-based oil, the polymerization may be performed directly in said oil, which thus also acts as synthesis solvent. The monomers should also be soluble therein, as should the free-radical initiator, and the polymer of the particles which is obtained should be insoluble therein.

The monomers are preferably present in the synthesis solvent, before polymerization, in a proportion of 5-20% by weight. The total amount of monomers may be present in the solvent before the start of the reaction, or part of the monomers may be added gradually as the polymerization reaction proceeds.

The free-radical initiator may especially be azobisisobutyronitrile or tert-butyl peroxy-2-ethylhexanoate.

The polymerization may be performed at a temperature ranging from 70 to 110° C.

The polymer particles are surface-stabilized, when they are formed during the polymerization, by means of the stabilizer.

The stabilization may be performed by any known means, and in particular by direct addition of the stabilizer, during the polymerization.

The stabilizer is preferably also present in the mixture before polymerization of the monomers of the polymer of the particles. However, it is also possible to add it continuously, especially when the monomers of the polymer of the particles are also added continuously.

From 10% to 30% by weight and preferably from 15% to 25% by weight of stabilizer may be used relative to the total weight of monomers used (stabilizer+polymer of the particles).

The polymer particle dispersion advantageously comprises from 30% to 65% by weight and preferably from 40% to 60% by weight of solids, relative to the total weight of the dispersion.

Moreover, the composition according to the invention advantageously comprises a content of surface-stabilized polymer particles of between 5% and 55% by weight and more specifically between 5% and 50% by weight, preferably between 8% and 45% by weight and even more preferably between 10% and 40% by weight relative to the weight of composition.

Plasticizer

According to a particular embodiment of the invention, the composition comprises at least one plasticizer.

In the case where the polymer particles are provided in the form of a dispersion, the plasticizer is then advantageously present in said oily dispersion.

The plasticizer(s) may be chosen from tri-n-butyl citrate, tripropylene glycol monomethyl ether (INCI name: PPG-3 methyl ether) and trimethyl pentaphenyl trisiloxane (sold under the name Dow Corning PH-1555 HRI Cosmetic Fluid by the company Dow Corning). These plasticizers make it possible to improve the mechanical strength of the polymer film.

The plasticizer may be present in a content ranging from 2% to 50% by weight relative to the total weight of the polymer particles, preferably from 2% to 40% by weight and even more particularly less than 20% by weight relative to the weight of the composition.

Ethylcellulose

As indicated previously, the composition according to the invention comprises at least alkylcellulose, the alkyl residue of which comprises between 2 and 6 carbon atoms and preferably between 2 and 3 carbon atoms, and better still a composition according to the invention comprises ethylcellulose.

According to a particularly preferred embodiment, the alkylcellulose (the alkyl residue of which preferably comprises between 2 and 6 carbon atoms, preferentially ethylcellulose) may be present in a composition according to the invention in a (solids) content ranging from 1% to 8% by weight and preferably from 2.5% to 6% by weight of alkylcellulose solids relative to the total weight of said composition.

The alkylcellulose is a cellulose alkyl ether comprising a chain formed from β-anhydroglucose units linked together via acetal bonds. Each anhydroglucose unit contains three replaceable hydroxyl groups, all or some of these hydroxyl groups being able to react according to the following reaction:

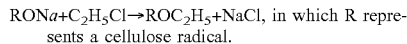
$RONa+C_2H_5Cl \rightarrow ROC_2H_5+NaCl$, in which R represents a cellulose radical.

Advantageously, the alkylcellulose may be chosen from ethylcellulose and propylcellulose.

According to a particularly preferred embodiment, the alkylcellulose may be ethylcellulose.

It is a cellulose ethyl ether.

Total substitution of the three hydroxyl groups would lead, for each anhydroglucose unit, to a degree of substitution of 3, in other words to a content of alkoxy groups of 54.88%.

The ethylcellulose polymers used in a cosmetic composition according to the invention are preferentially polymers with a degree of substitution with ethoxy groups ranging from 2.5 to 2.6 per anhydroglucose unit, in other words comprising a content of ethoxy groups ranging from 44% to 50%.

According to a preferred mode, the alkylcellulose (preferably ethylcellulose) may be used in a composition of the invention in the form of particles dispersed in an aqueous phase, like a dispersion of latex or pseudolatex type. The techniques for preparing these latex dispersions are well known to those skilled in the art.

The product sold by the company FMC Biopolymer under the name Aquacoat ECD-30, which consists of a dispersion of ethylcellulose stabilized with sodium lauryl sulfate and cetyl alcohol, is most particularly suitable for use as an aqueous dispersion of ethylcellulose.

Water

The composition according to the invention comprises water.

The water content usually ranges between 10% and 50% by weight relative to the weight of the composition and preferably between 10% and 40% by weight relative to the weight of the composition.

The composition according to the invention may be in the form of an oil-in-water or water-in-oil emulsion, but preferably a water-in-oil emulsion.

Water-Soluble Compound

The composition according to the invention may also comprise at least one water-soluble compound.

In the present invention, the term "water-soluble compound" denotes a compound that is liquid at room temperature and water-miscible (miscibility with water of greater than 50% by weight at 25° C. and atmospheric pressure).

The water-soluble compounds that may be used in the compositions according to the invention may also be volatile.

Among the water-soluble compounds that may be used in the compositions in accordance with the invention, mention may be made especially of monoalcohols, which are preferably saturated, containing less than 8 carbon atoms and preferably less than 5 carbon atoms, such as ethanol, isopropanol and butanol; saturated or unsaturated, linear or branched $C_2$-$C_8$ and preferably $C_3$-$C_6$ polyols, comprising from 2 to 6 hydroxyl groups, and preferably glycerol, ethylene glycol, propylene glycol, 1,3-butylene glycol, dipropylene glycol or diglycerol, and a mixture thereof.

Preferably, the content of water-soluble compound(s), if the composition according to the invention comprises any, ranges from 0.2% to 10% by weight and preferably from 0.2% to 8% by weight, relative to the weight of the composition.

Surfactants

As indicated previously, the composition comprises at least one surfactant that promotes the production of a reverse emulsion (water-in-oil). Preferably, the composition comprises at least one surfactant whose HLB (hydrophilic/lipophilic balance) is less than 7.

Preferably, the composition thus comprises at least one hydrocarbon-based or silicone surfactant, or a mixture thereof.

More particularly, the surfactant is chosen from fatty acid esters of polyols; alkyl or alkoxy dimethicone copolyols bearing an alkyl or alkoxy chain that is pendent or at the end of the silicone backbone, containing, for example, from 6 to 22 carbon atoms; polymers of the polyoxyalkylenated glycol fatty acid ester type, and mixtures thereof.

As regards the hydrocarbon-based surfactants of the type such as fatty acid esters of polyols, mention may be made in particular of fatty acid mono-, di-, tri- or sesqui-esters, in particular polyol laurates, oleates, stearates or isostearates. These polyols are more particularly chosen from sorbitol, glycerol, polyglycerols and polyethylene glycols, or mixtures thereof. Mention may be made most particularly of sorbitol or glyceryl mono-, di-, tri- or sesqui-oleates or stearates and glyceryl or polyethylene glycol laurates.

Mention may also be made of glycerol and/or sorbitan esters, for example the polyglyceryl-3 diisostearate sold under the name Lameform TGI by the company Cognis, polyglyceryl-4 isostearate, such as the product sold under the name Isolan GI 34 by the company Goldschmidt, sorbitan isostearate, such as the product sold under the name Arlacel 987 by the company ICI, sorbitan glyceryl isostearate, such as the product sold under the name Arlacel 986 by the company ICI, and mixtures thereof.

As another hydrocarbon-based surfactant that may be used in the invention to obtain a W/O emulsion, mention may be made of polymers of the polyoxyalkylenated glycol fatty acid ester type promoting water-in-oil emulsions.

The fatty acid ester of said polymer is preferably polyhydroxylated. In particular, this polymer is a block polymer, preferably of ABA structure, comprising poly(hydroxylated ester) blocks and polyethylene glycol blocks.

The fatty acid ester of said emulsifying polymer as defined above generally bears a chain comprising from 12 to 20 carbon atoms and preferably from 14 to 18 carbon atoms. The esters may be chosen especially from oleates, palmitates and stearates.

The polyethylene glycol blocks of said emulsifying polymer as defined above preferably comprise from 4 to 50 mol of ethylene oxide and more preferably from 20 to 40 mol of ethylene oxide.

A polymeric surfactant that is particularly suitable for preparing the compositions of the invention is polyethylene glycol dipolyhydroxystearate with 30 OE, sold under the trade name Arlacel P 135 by the company ICI.

As regards the silicone surfactants, the ones that are particularly suitable for use are surfactants of the alkyl or alkoxy dimethicone copolyol type bearing an alkyl or alkoxy chain that is pendent or at the end of the silicone backbone, for example containing from 6 to 22 carbon atoms.

Advantageously, the surfactant may be a $C_8$-$C_{22}$ alkyl dimethicone copolyol, i.e. an oxypropylenated and/or oxyethylenated polymethyl($C_8$-$C_{22}$)alkyldimethylmethylsiloxane.

The $C_8$-$C_{22}$ alkyl dimethicone copolyol is advantageously a compound of formula (I) below:

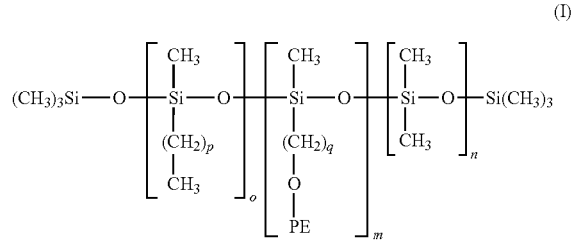

in which:
PE represents $(-C_2H_4O)_x-(C_3H_6O)_y-R$, R being chosen from a hydrogen atom and an alkyl radical of 1 to 4 carbon atoms, x ranging from 0 to 100 and y ranging from 0 to 80, x and y not simultaneously being 0
m ranging from 1 to 40
n ranging from 10 to 200
o ranging from 1 to 100
p ranging from 7 to 21
q ranging from 0 to 4.

Preferably, in formula (I), R represents a hydrogen atom, m ranges from 1 to 10; n ranges from 10 to 100; o ranges from 1 to 30; p is 15 and q is 3.

Preferably, as $C_8$-$C_{22}$ alkyl dimethicone copolyol, use is made of cetyl dimethicone copolyol, especially the product whose INCI name is Cetyl PEG/PPG-10/1 Dimethicone, for instance the product sold under the name Abil EM-90 by the company Evonik Goldschmidt.

Use may also be made of compounds of formula (II) below:

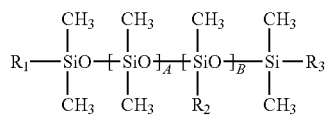

in which:
$R_1$, $R_2$ and $R_3$, independently of each other, represent a $C_1$-$C_6$ alkyl radical or a radical $-(CH_2)_x-(OCH_2CH_2)_y-(OCH_2CH_2CH_2)_z-OR_4$, at least one radical $R_1$, $R_2$ or $R_3$ not being an alkyl radical; $R_4$ being a hydrogen, a $C_1$-$C_3$ alkyl radical or a $C_2$-$C_4$ acyl radical;

A is an integer ranging from 0 to 200;
B is an integer ranging from 0 to 50; on condition that A and B are not simultaneously equal to zero;
x is an integer ranging from 1 to 6;
y is an integer ranging from 1 to 30; and
z is an integer ranging from 0 to 5.

According to one preferred embodiment, in the compound of formula (II), $R_1=R_3$=methyl radical, x is an integer ranging from 2 to 6 and y is an integer ranging from 4 to 30. $R_4$ is in particular a hydrogen.

Examples of compounds of formula (II) that may be mentioned include the compounds of formula (III):

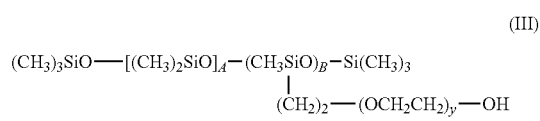

in which A is an integer ranging from 20 to 105, B is an integer ranging from 2 to 10 and y is an integer ranging from 10 to 20.

Examples of silicone compounds of formula (II) that may also be mentioned include the compounds of formula (IV):

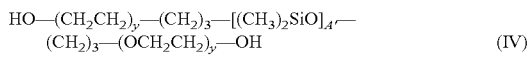

in which A' and y are integers ranging from 10 to 20.

Dimethicone copolyols that may be used include those sold under the names DC 5329, DC 7439-146, DC 2-5695 and Q4-3667 by the company Dow Corning; KF-6013, KF-6015, KF-6016, KF-6017 and KF-6028 by the company Shin-Etsu.

The compounds DC 5329, DC 7439-146 and DC 2-5695 are compounds of formula (III) in which, respectively, A is 22, B is 2 and y is 12; A is 103, B is 10 and y is 12; A is 27, B is 3 and y is 12.

According to a particular embodiment, the silicone surfactant may be PEG polydimethylsiloxyethyl dimethicone, sold in particular by the company Shin-Etsu under the reference KF-6028, PEG-10 dimethicone sold in particular by the company Shin-Etsu under the reference KF-6017, and mixtures thereof.

Preferably, the composition comprises at least one silicone surfactant such as the $C_8$-$C_{22}$ alkyl dimethicone copolyols of formula (I). More advantageously, said silicone surfactant is cetyl dimethicone copolyol, especially the product whose INCI name is Cetyl PEG/PPG-10/1 Dimethicone, for instance the product sold under the name Abil EM-90 by the company Evonik Goldschmidt.

Preferably, according to this embodiment, the composition also comprises at least one cosurfactant chosen from polyol alkyl esters, preferably from glycerol and/or sorbitan esters. Preferably, the cosurfactant is chosen from polyglyceryl-3 diisostearate, polyglyceryl-4 isostearate, sorbitan isostearate and sorbitan glyceryl isostearate, and mixtures thereof.

Preferably, the cosurfactant is polyglyceryl-4 isostearate, such as the product sold under the name Isolan GI 34 by the company Goldschmidt.

Advantageously, the content of surfactant(s) in the composition ranges from 0.2% to 10% by weight, or even from 0.5% to 7% by weight, relative to the weight of the composition.

Mineral Thickener

The composition according to the invention may also comprise at least one mineral thickener chosen from optionally modified clays and optionally modified silicas, or mixtures thereof.

More particularly, the content of mineral thickener represents from 0.2% to 15% by weight, expressed as active material, and preferably from 0.5% to 7% by weight, relative to the weight of the composition.

In accordance with an advantageous embodiment of the invention, the content of mineral thickener is such that the weight ratio (expressed as active material) of polymer particles/thickener ranges from 0.5 to 80, preferably from 5 to 50 and more particularly from 10 to 30.

i) Optionally Modified Clays

Clays are silicates containing a cation that may be chosen from calcium, magnesium, aluminium, sodium, potassium and lithium cations, and mixtures thereof.

Examples of such products that may be mentioned include clays of the smectite family, and also of the vermiculite, stevensite and chlorite families. These clays can be of natural or synthetic origin.

Mention may more particularly be made of smectites, such as saponites, hectorites, montmorillonites, bentonites or beidellite and in particular synthetic hectorites (also known as laponites), such as the products sold by Laporte under the names Laponite XLG, Laponite RD and Laponite RDS (these products are sodium magnesium silicates and in particular sodium lithium magnesium silicates); bentonites, such as the product sold under the name Bentone HC by Rheox; magnesium aluminium silicates, which are in particular hydrated, such as the products sold by Vanderbilt Company under the name Veegum Ultra, Veegum HS or Veegum DGT, or also calcium silicates and in particular that in synthetic form sold by the company under the name Micro-Cel C.

Preferably, use is made of organophilic clays, more particularly modified clays, such as montmorillonite, bentonite, hectorite, attapulgite and sepiolite, and mixtures thereof. The clay is preferably a bentonite or a hectorite.

These clays are modified with a chemical compound chosen from quaternary amines, tertiary amines, amine acetates, imidazolines, amine soaps, fatty sulfates, alkylarylsulfonates and amine oxides, and mixtures thereof.

Mention may thus be made of hectorites modified with a quaternary amine, more specifically with a $C_{10}$ to $C_{22}$ fatty acid ammonium halide, such as a chloride, such as hectorite modified with distearyldimethylammonium chloride (CTFA name: Disteardimonium hectorite), for instance the product sold under the name Bentone 38V®, Bentone 38V CG or Bentone EW CE by the company Elementis, or stearalkonium hectorites, such as Bentone 27 V.

Mention may also be made of quaternium-18 bentonites, such as those sold under the names Bentone 34 by the company Elementis, Tixogel VP by the company United Catalyst and Claytone 40 by the company Southern Clay; stearalkonium bentonites, such as those sold under the names Tixogel LG by the company United Catalyst and Claytone AF and Claytone APA by the company Southern Clay; or quaternium-18/benzalkonium bentonites, such as that sold under the name Claytone HT by the company Southern Clay.

According to a preferred embodiment, the thickener is chosen from organophilic modified clays, in particular organophilic modified hectorites, in particular modified with benzyldimethylammonium stearate chloride or with distearyldimethylammonium chloride.

In accordance with one variant of the invention, the content of optionally modified clay ranges from 0.2% to 10% by weight relative to the weight of the composition, and preferably from 0.5% to 5% by weight relative to the weight of the composition. These percentages are expressed as active material.

ii) Optionally Modified Silicas

Mention may also be made of fumed silica optionally subjected to a hydrophobic surface treatment, the particle size of which is less than 1 μm. Specifically, it is possible to chemically modify the surface of the silica, by chemical reaction generating a reduced number of silanol groups present at the surface of the silica. It is especially possible to substitute silanol groups with hydrophobic groups: a hydrophobic silica is then obtained. The hydrophobic groups may be:

trimethylsiloxyl groups, which are obtained especially by treating fumed silica in the presence of hexamethyldisilazane. Silicas thus treated are known as "Silica silylate" according to the CTFA (6th edition, 1995). They are sold, for example, under the references Aerosil R812® by the company Degussa, and Cab-O-Sil TS-530® by the company Cabot;

dimethylsilyloxyl or polydimethylsiloxane groups, which are obtained in particular by treating fumed silica in the presence of polydimethylsiloxane or dimethyldichlorosilane. Silicas thus treated are known as "Silica dimethyl silylate" according to the CTFA (6th edition, 1995). They are sold, for example, under the references Aerosil R972® and Aerosil R974® by the company Degussa, and Cab-O-Sil TS-610® and Cab-O-Sil TS-720® by the company Cabot.

The hydrophobic fumed silica in particular has a particle size that may be nanometric to micrometric, for example ranging from about 5 to 200 nm.

The composition according to the invention may comprise or comprises at least silica aerogel particles.

Silica aerogels are porous materials obtained by replacing (by drying) the liquid component of a silica gel with air.

They are generally synthesized via a sol-gel process in a liquid medium and then dried, usually by extraction with a supercritical fluid, the one most commonly used being supercritical $CO_2$. This type of drying makes it possible to avoid shrinkage of the pores and of the material. The sol-gel process and the various drying processes are described in detail in Brinker C J., and Scherer G. W., Sol-Gel Science: New York: Academic Press, 1990.

The hydrophobic silica aerogel particles used in the present invention have a specific surface area per unit mass ($S_M$) ranging from 500 to 1500 m$^2$/g, preferably from 600 to 1200 m$^2$/g and better still from 600 to 800 m$^2$/g, and a size expressed as the volume mean diameter (D[0.5]) ranging from 1 to 1500 μm, better still from 1 to 1000 μm, preferably from 1 to 100 μm, in particular from 1 to 30 μm, more preferably from 5 to 25 μm, better still from 5 to 20 μm and even better still from 5 to 15 μm.

According to one embodiment, the hydrophobic silica aerogel particles used in the present invention have a size expressed as volume-mean diameter (D[0.5]) ranging from 1 to 30 μm, preferably from 5 to 25 μm, better still from 5 to 20 μm and even better still from 5 to 15 μm.

The specific surface area per unit mass may be determined by the nitrogen absorption method, known as the BET (Brunauer-Emmett-Teller) method, described in The Journal of the American Chemical Society, vol. 60, page 309, February 1938 and corresponding to international standard ISO 5794/1 (appendix D). The BET specific surface area corresponds to the total specific surface area of the particles under consideration.

The sizes of the silica aerogel particles may be measured by static light scattering using a commercial particle size analyser such as the MasterSizer 2000 machine from Malvern. The data are processed on the basis of the Mie scattering theory. This theory, which is exact for isotropic particles, makes it possible to determine, in the case of non-spherical particles, an "effective" particle diameter. This theory is especially described in the publication by Van de Hulst, H. C., *Light Scattering by Small Particles*, Chapters 9 and 10, Wiley, New York, 1957.

According to an advantageous embodiment, the hydrophobic silica aerogel particles used in the present invention have a specific surface area per unit mass ($S_M$) ranging from 600 to 800 $m^2/g$ and a size expressed as the volume mean diameter (D[0.5]) ranging from 5 to 20 μm and even better still from 5 to 15 μm.

The silica aerogel particles used in the present invention can advantageously exhibit a tapped density a ranging from 0.02 $g/cm^3$ to 0.10 $g/cm^3$, preferably from 0.03 $g/cm^3$ to 0.08 $g/cm^3$ and preferably from 0.05 $g/cm^3$ to 0.08 $g/cm^3$.

In the context of the present invention, this density, known as the tapped density, may be assessed according to the following protocol:

40 g of powder are poured into a measuring cylinder; the measuring cylinder is then placed on a Stay 2003 machine from Stampf Volumeter; the measuring cylinder is then subjected to a series of 2500 tapping actions (this operation is repeated until the difference in volume between two consecutive tests is less than 2%); the final volume Vf of tapped powder is then measured directly on the measuring cylinder. The tapped density is determined by the ratio m/Vf, in this instance 40/Vf (Vf being expressed in $cm^3$ and m in g).

According to a preferred embodiment, the hydrophobic silica aerogel particles used in the present invention have a specific surface area per unit of volume $S_V$ ranging from 5 to 60 $m^2/cm^3$, preferably from 10 to 50 $m^2/cm^3$ and better still from 15 to 40 $m^2/cm^3$.

The specific surface area per unit of volume is given by the relationship: $S_V = S_M \times \sigma$, where σ is the tapped density, expressed in $g/cm^3$, and $S_M$ is the specific surface area per unit mass, expressed in $m^2/g$, as defined above.

Preferably, the hydrophobic silica aerogel particles according to the invention have an oil-absorbing capacity, measured at the wet point, ranging from 5 to 18 ml/g, preferably from 6 to 15 ml/g and better still from 8 to 12 ml/g.

The absorbing capacity measured at the wet point, noted Wp, corresponds to the amount of oil that needs to be added to 100 g of particles in order to obtain a homogeneous paste.

It is measured according to what is known as the wet point method or the method for determining the oil uptake of a powder described in standard NF T 30-022. It corresponds to the amount of oil adsorbed onto the available surface of the powder and/or absorbed by the powder by measurement of the wet point, described below:

An amount m=2 g of powder is placed on a glass plate, and the oil (isononyl isononanoate) is then added dropwise. After addition of 4 to 5 drops of oil to the powder, mixing is carried out using a spatula, and addition of oil is continued until conglomerates of oil and powder have formed. From this point, the oil is added at the rate of one drop at a time and the mixture is subsequently triturated with the spatula. The addition of oil is stopped when a firm, smooth paste is obtained. This paste must be able to be spread on the glass plate without cracking or forming lumps. The volume Vs (expressed in ml) of oil used is then noted.

The oil uptake corresponds to the ratio Vs/m.

The aerogels used according to the present invention are hydrophobic silica aerogels, preferably of silyl silica (INCI name: silica silylate).

The term "hydrophobic silica" means any silica whose surface is treated with silylating agents, for example halogenated silanes such as alkylchlorosilanes, siloxanes, in particular dimethylsiloxanes such as hexamethyldisiloxane, or silazanes, so as to functionalize the OH groups with silyl groups Si—Rn, for example trimethylsilyl groups.

As regards the preparation of hydrophobic silica aerogel particles that have been surface-modified by silylation, reference may be made to document U.S. Pat. No. 7,470,725.

Use will preferably be made of hydrophobic silica aerogel particles surface-modified with trimethylsilyl groups.

As hydrophobic silica aerogels that may be used in the invention, examples that may be mentioned include the aerogel sold under the name VM-2260 (INCI name: Silica silylate), by the company Dow Corning, the particles of which have a mean size of about 1000 microns and a specific surface area per unit of mass ranging from 600 to 800 $m^2/g$.

Mention may also be made of the aerogels sold by the company Cabot under the references Aerogel TLD 201, Aerogel OGD 201, Aerogel TLD 203, Enova® Aerogel MT 1100 and Enova Aerogel MT 1200.

Use will preferably be made of the aerogel sold under the name VM-2270 (INCI name: Silica silylate) by the company Dow Corning, the particles of which have an average size ranging from 5-15 microns and a specific surface area per unit of mass ranging from 600 to 800 $m^2/g$.

Preferably, when the composition comprises at least one thickener chosen from optionally modified silicas, these silicas are chosen from hydrophobic silica aerogel particles.

In accordance with one variant of the invention, the content of optionally modified silica ranges from 0.5% to 15% by weight and preferably from 1% to 7% by weight relative to the weight of the composition. These values are expressed as weight of active material.

Preferably, the mineral thickeners are chosen from lipophilic (organophilic) clays, in particular modified hectorites; hydrophobic-treated fumed silica; hydrophobic silica aerogels, or mixtures thereof.

Preferably, the composition comprises at least one organophilic modified clay or at least one hydrophobic modified silica, in particular hydrophobic silica aerogels.

Block Hydrocarbon-Based Copolymer

As indicated previously, the composition according to the invention comprises at least one hydrocarbon-based copolymer bearing amorphous blocks, obtained by polymerization of at least one monomer of unsaturated hydrocarbon type comprising 2 to 5 carbon atoms and containing one or two ethylenic unsaturations.

These block hydrocarbon-based copolymers are preferably soluble or dispersible in the oily phase.

They may especially be of diblock, triblock, multiblock, radial or starburst type, or mixtures thereof.

Such block hydrocarbon-based copolymers are described, for example, in patent application US 2002/005 562 and in U.S. Pat. No. 5,221,534.

The copolymer may contain at least one block whose glass transition temperature is preferably less than 20° C., preferably less than or equal to 0° C., preferably less than or equal to −20° C. and more preferably less than or equal to −40° C. The glass transition temperature of said block may be between −150° C. and 20° C., especially between −100° C. and 0° C.

The term "amorphous polymer" means a polymer which has no crystalline form.

The monomer of unsaturated hydrocarbon type comprising 2 to 5 carbon atoms and having one or two ethylenic unsaturations may especially be an elastomeric ethylenically unsaturated monomer.

As examples of monomers of unsaturated hydrocarbon type comprising 2 to 5 unsaturated carbon atoms, mention may be made of ethylene, propylene, butadiene, isoprene or pentadiene.

Advantageously, the block hydrocarbon-based copolymer is an amorphous block copolymer of styrene and of hydrocarbon monomer(s) comprising 2 to 5 carbon atoms and comprising one or two ethylenic unsaturations.

Block copolymers comprising at least one styrene block and at least one block comprising units chosen from butadiene, ethylene, propylene, butylene and isoprene or a mixture thereof are especially preferred.

According to a preferred embodiment, the block hydrocarbon-based copolymer is hydrogenated to reduce the residual ethylenic unsaturations after polymerization of the monomers.

In particular, the block hydrocarbon-based copolymer is an optionally hydrogenated copolymer bearing styrene blocks and ethylene/$C_3$-$C_4$ alkylene blocks or isoprene blocks.

According to a preferred embodiment, the composition according to the invention comprises at least one diblock copolymer, which is preferably hydrogenated, preferably chosen from styrene-ethylene/propylene copolymers, styrene-ethylene/butadiene copolymers, styrene-ethylene/butylene copolymers and styrene-isoprene copolymers. Diblock polymers are especially sold under the name Kraton® G1701E by the company Kraton Polymers.

According to another preferred embodiment, the composition according to the invention comprises at least one triblock copolymer, which is preferably hydrogenated, preferably chosen from styrene-ethylene/propylene-styrene copolymers, styrene-ethylene/butadiene-styrene copolymers, styrene-isoprene-styrene copolymers and styrene-butadiene-styrene copolymers. Triblock polymers are especially sold under the names Kraton® G1650, Kraton® D1101, Kraton® D1102 and Kraton® D1160 by the company Kraton Polymers.

According to one embodiment of the present invention, the hydrocarbon-based block copolymer is a styrene-ethylene/butylene-styrene triblock copolymer.

According to a preferred embodiment of the invention, use may be made especially of a mixture of a styrene-butylene/ethylene-styrene triblock copolymer and of a styrene-ethylene/butylene diblock copolymer, especially those sold under the name Kraton® G1657M by the company Kraton Polymers.

According to another preferred embodiment, the composition according to the invention comprises a mixture of hydrogenated styrene-butylene/ethylene-styrene triblock copolymer and of hydrogenated ethylene-propylene-styrene starburst polymer, such a mixture possibly being especially in isododecane or in another oil. Such mixtures are sold, for example, by the company Penreco under the trade names Versagel® M5960 and Versagel® M5670.

Advantageously, a diblock copolymer such as those described previously is used as block hydrocarbon-based copolymer, in particular a styrene-ethylene/propylene diblock copolymer, or a mixture of diblock and triblock, as described previously, such as mixture of a styrene-butylene/ethylene-styrene triblock copolymer and of a styrene-ethylene/butylene diblock copolymer.

The block hydrocarbon-based copolymer(s) may be present in a content ranging from 2.5% to 15% by weight, relative to the total weight of the composition, preferably ranging from 2.5% to 8% by weight, relative to the total weight of the composition.

Additional Silicone Oils

The composition according to the invention may also comprise at least one additional volatile or non-volatile silicone oil.

The term "silicone oil" means an oil containing at least one silicon atom, and especially containing Si—O groups.

As additional volatile silicone oils that are suitable for use, examples that may be mentioned include volatile linear or cyclic silicone oils, especially those with a viscosity≤8 centistokes ($8 \times 10^{-6}$ m$^2$/s) and especially containing from 2 to 7 silicon atoms, these silicones optionally comprising alkyl or alkoxy groups containing from 1 to 10 carbon atoms.

As volatile silicone oils that may be used, mention may be made especially of octamethylcyclotetrasiloxane, cyclopentadimethylsiloxane, decamethylcyclopenta-siloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

As non-volatile silicone oils, mention may be made of non-phenyl non-volatile silicone oils, for instance polydimethylsiloxanes (PDMS), PDMSs comprising aliphatic groups, in particular alkyl or alkoxy, which are pendent and/or at the end of the silicone chain; these groups each comprising from 2 to 24 carbon atoms. An example that may be mentioned is cetyl dimethicone sold under the commercial reference Abil Wax 9801 from Evonik Goldschmidt.

Non-volatile phenyl silicone oils optionally comprising one or more dimethicone fragments (—(CH3)2-SiO—) are also suitable for use, for instance phenyl trimethicones, phenyl dimethicones, phenyltrimethylsiloxydiphenylsiloxanes, diphenyl dimethicones and trimethylpentaphenyltrisiloxane, and mixtures thereof.

If the composition comprises any, the content of additional silicone oil(s) is between 1% and 15% by weight relative to the weight of the composition.

Preferably, the composition does not comprise more than 10% by weight and preferably not more than 5% by weight of additional non-volatile oil, relative to the weight of the composition.

Waxes

The composition according to the invention may optionally comprise at least one wax.

For the purposes of the present invention, the term "wax" means a lipophilic compound, which is solid at room temperature (25° C.), with a reversible solid/liquid change of state, which has a melting point of greater than or equal to 30° C. that may be up to 120° C.

The melting point of the wax may be measured using a differential scanning calorimeter (DSC), for example the calorimeter sold under the name DSC 30 by the company Mettler.

The waxes may be hydrocarbon-based waxes, fluoro waxes and/or silicone waxes, and may be of plant, mineral, animal and/or synthetic origin. In particular, the waxes have a melting point of greater than 25° C. and better still greater than 45° C.

Hydrocarbon-based waxes, for instance beeswax, lanolin wax or Chinese insect waxes; rice wax, carnauba wax, candelilla wax, ouricury wax, esparto grass wax, cork fibre wax, sugar cane wax, Japan wax and sumac wax; montan wax, microcrystalline waxes, paraffins and ozokerite; polyethylene waxes, the waxes obtained by Fisher-Tropsch synthesis and waxy copolymers, and also esters thereof, may especially be used.

Mention may also be made of waxes obtained by catalytic hydrogenation of animal or plant oils containing linear or branched $C_8$-$C_{32}$ fatty chains.

Among these waxes that may in particular be mentioned are hydrogenated jojoba oil, isomerized jojoba oil such as the trans-isomerized partially hydrogenated jojoba oil manufactured or sold by the company Desert Whale under the commercial reference Iso-Jojoba-500, hydrogenated sunflower oil, hydrogenated castor oil, hydrogenated coconut oil, hydrogenated lanolin oil and bis(1,1,1-trimethylolpropane) tetrastearate sold under the name Hest 2T-4S by the company Heterene, bis(1,1,1-trimethylolpropane) tetrabehenate sold under the name Hest 2T-4B by the company Heterene.

Mention may also be made of silicone waxes, for instance alkyl or alkoxy dimethicones containing from 16 to 45 carbon atoms, polypropylsilsesquioxane waxes (as described in patent WO 2005/100444), in particular with the $C_{30}$-$C_{45}$ alkyldimethylsilyl polypropylsilsesquioxane compound commercially available from Dow Corning under the brand name SW-8005 C30 Resin Wax; fluoro waxes, and preferably silicone-based waxes.

The wax obtained by hydrogenation of olive oil esterified with the stearyl alcohol, sold under the name Phytowax Olive 18 L 57 or else the waxes obtained by hydrogenation of castor oil esterified with cetyl alcohol, sold under the names Phytowax Castor 16L64 and 22L73 by the company Sophim, may also be used. Such waxes are described in patent application FR-A-2 792 190.

If the composition comprises one or more waxes, their content represents from 0.4% to 20% by weight relative to the weight of the composition, and preferably from 0.5% to 5% by weight relative to the weight of the composition.

Pigments

The term "pigments" should be understood as meaning white or coloured, inorganic (mineral) or organic particles, which are insoluble in the liquid organic phase, and which are intended to colour and/or opacify the composition and/or the deposit produced with the composition.

The pigments may be chosen from mineral pigments, organic pigments and composite pigments (i.e. pigments based on mineral and/or organic materials).

The pigments may be chosen from monochromatic pigments, lakes and pigments with an optical effect, for instance goniochromatic pigments and nacres.

If the composition comprises any, their content ranges from 0.1% to 10% by weight relative to the weight of the composition, and preferably from 0.5% to 7% by weight relative to the weight of the composition.

The mineral pigments may be chosen from metal oxide pigments, chromium oxides, iron oxides (black, yellow, red), titanium dioxide, zinc oxides, cerium oxides, zirconium oxides, chromium hydrate, manganese violet, Prussian blue, ultramarine blue, ferric blue, metal powders such as aluminium powders and copper powder, and mixtures thereof.

Organic lakes are organic pigments formed from a dye attached to a substrate.

The lakes, which are also known as organic pigments, may be chosen from the materials below, and mixtures thereof:
  cochineal carmine;
  organic pigments of azo dyes, anthraquinone dyes, indigoid dyes, xanthene dyes, pyrene dyes, quinoline dyes, triphenylmethane dyes or fluoran dyes.

Among the organic pigments that may in particular be mentioned are those known under the following names: D&C Blue No. 4, D&C Brown No. 1, D&C Green No. 5, D&C Green No. 6, D&C Orange No. 4, D&C Orange No. 5, D&C Orange No. 10, D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Violet No. 2, D&C Yellow No. 7, D&C Yellow No. 8, D&C Yellow No. 10, D&C Yellow No. 11, FD&C Blue No. 1, FD&C Green No. 3, FD&C Red No. 40, FD&C Yellow No. 5, FD&C Yellow No. 6;
  the organic lakes may be insoluble sodium, potassium, calcium, barium, aluminium, zirconium, strontium or titanium salts of acidic dyes such as azo, anthraquinone, indigoid, xanthene, pyrene, quinoline, triphenylmethane or fluoran dyes, these dyes possibly comprising at least one carboxylic or sulfonic acid group.

The organic lakes may also be supported on an organic support such as rosin or aluminium benzoate, for example.

Among the organic lakes, mention may be made in particular of those known under the following names: D&C Red No. 2 Aluminium lake, D&C Red No. 3 Aluminium lake, D&C Red No. 4 Aluminium lake, D&C Red No. 6 Aluminium lake, D&C Red No. 6 Barium lake, D&C Red No. 6 Barium/Strontium lake, D&C Red No. 6 Strontium lake, D&C Red No. 6 Potassium lake, D&C Red No. 7 Aluminium lake, D&C Red No. 7 Barium lake, D&C Red No. 7 Calcium lake, D&C Red No. 7 Calcium/Strontium lake, D&C Red No. 7 Zirconium lake, D&C Red No. 8 Sodium lake, D&C Red No. 9 Aluminium lake, D&C Red No. 9 Barium lake, D&C Red No. 9 Barium/Strontium lake, D&C Red No. 9 Zirconium lake, D&C Red No. 10 Sodium lake, D&C Red No. 19 Aluminium lake, D&C Red No. 19 Barium lake, D&C Red No. 19 Zirconium lake, D&C Red No. 21 Aluminium lake, D&C Red No. 21 Zirconium lake, D&C Red No. 22 Aluminium lake, D&C Red No. 27 Aluminium lake, D&C Red No. 27 Aluminium/Titanium/Zirconium lake, D&C Red No. 27 Barium lake, D&C Red No. 27 Calcium lake, D&C Red No. 27 Zirconium lake, D&C Red No. 28 Aluminium lake, D&C Red No. 30 lake, D&C Red No. 31 Calcium lake, D&C Red No. 33 Aluminium lake, D&C Red No. 34 Calcium lake, D&C Red No. 36 lake, D&C Red No. 40 Aluminium lake, D&C Blue No. 1 Aluminium lake, D&C Green No. 3 Aluminium lake, D&C Orange No. 4 Aluminium lake, D&C Orange No. 5 Aluminium lake, D&C Orange No. 5 Zirconium lake, D&C Orange No. 10 Aluminium lake, D&C Orange No. 17 Barium lake, D&C Yellow No. 5 Aluminium lake, D&C Yellow No. 5 Zirconium lake, D&C Yellow No. 6 Aluminium lake, D&C Yellow No. 7 Zirconium lake, D&C Yellow No. 10 Aluminium lake, FD&C Blue No. 1 Aluminium lake, FD&C Red No. 4 Aluminium lake, FD&C Red No. 40 Aluminium lake, FD&C Yellow No. 5 Aluminium lake, FD&C Yellow No. 6 Aluminium lake.

Mention may also be made of liposoluble dyes, such as, for example, Sudan Red, DC Red 17, DC Green 6, β-carotene, soybean oil, Sudan Brown, DC Yellow 11, DC Violet 2, DC Orange 5 and quinoline yellow.

The chemical materials corresponding to each of the organic dyestuffs mentioned previously are mentioned in the publication "International Cosmetic Ingredient Dictionary and Handbook", 1997 edition, pages 371 to 386 and 524 to 528, published by The Cosmetic, Toiletries and Fragrance Association, the content of which is incorporated into the present patent application by reference.

The pigments may also have been subjected to a hydrophobic treatment.

The hydrophobic treatment agent may be chosen from silicones such as methicones, dimethicones, alkoxysilanes and perfluoroalkylsilanes; fatty acids such as stearic acid; metal soaps such as aluminium dimyristate, the aluminium salt of hydrogenated tallow glutamate, perfluoroalkyl phosphates, perfluoroalkylsilanes, perfluoroalkylsilazanes, polyhexafluoropropylene oxides, polyorganosiloxanes comprising perfluoroalkyl perfluoropolyether groups and amino acids; N-acylamino acids or salts thereof; lecithin, isopropyl triisostearyl titanate, and mixtures thereof.

The N-acylamino acids may comprise an acyl group containing from 8 to 22 carbon atoms, for instance a 2-ethylhexanoyl, caproyl, lauroyl, myristoyl, palmitoyl, stearoyl or cocoyl group. The salts of these compounds may be the aluminium, magnesium, calcium, zirconium, zinc, sodium or potassium salts. The amino acid may be, for example, lysine, glutamic acid or alanine.

The term "alkyl" mentioned in the compounds cited above especially denotes an alkyl group containing from 1 to 30 carbon atoms and preferably containing from 5 to 16 carbon atoms.

Hydrophobic-treated pigments are described especially in patent application EP-A-1 086 683.

Nacres

For the purposes of the present patent application, the term "nacre" means coloured particles of any form, which may or may not be iridescent, in particular produced by certain molluscs in their shell, or alternatively synthesized, and which have a colour effect via optical interference.

Examples of nacres that may be mentioned include nacreous pigments such as titanium mica coated with an iron oxide, mica coated with bismuth oxychloride, titanium mica coated with chromium oxide, titanium mica coated with an organic dye in particular of the abovementioned type, and also nacreous pigments based on bismuth oxychloride.

They may also be mica particles, at the surface of which are superposed at least two successive layers of metal oxides and/or of organic dyestuffs.

The nacres may more particularly have a yellow, pink, red, bronze, orange, brown, gold and/or coppery colour or glint.

As illustrations of nacres that may be introduced as interference pigments into the first composition, mention may be made of the gold-coloured nacres sold in particular by the company BASF under the name Brilliant gold 212G (Timica), Gold 222C (Cloisonne), Sparkle gold (Timica) and Monarch gold 233X (Cloisonne); the bronze nacres sold in particular by the company Merck under the name Bronze fine (17384) (Colorona) and Bronze (17353) (Colorona) and by the company BASF under the name Super bronze (Cloisonne); the orange nacres sold in particular by the company BASF under the name Orange 363C (Cloisonne) and by the company Merck under the name Passion orange (Colorona) and Matte orange (17449) (Microna); the brown tinted nacres sold in particular by the company Engelhard under the name Nu-antique copper 340XB (Cloisonne) and Brown CL4509 (Chroma-lite); the copper-tinted nacres sold in particular by the company BASF under the name Copper 340A (Timica); the red-tinted nacres sold in particular by the company Merck under the name Sienna fine (17386) (Colorona); the yellow-tinted nacres sold in particular by the company BASF under the name Yellow (4502) (Chromalite); the gold-tinted red nacres sold in particular by the company BASF under the name Sunstone G012 (Gemtone); the pink nacres sold in particular by the company BASF under the name Tan opal G005 (Gemtone); the gold-tinted black nacres sold in particular by the company BASF under the name Nu antique bronze 240 AB (Timica), the blue nacres sold in particular by the company Merck under the name Matte blue (17433) (Microna), the silvery-tinted white nacres sold in particular by the company Merck under the name Xirona Silver, and the golden-green pink-orange nacres sold in particular by the company Merck under the name Indian summer (Xirona), and mixtures thereof.

Goniochromatic Pigments

For the purposes of the present invention, the term "goniochromatic pigment" denotes a pigment which makes it possible to obtain, when the composition is spread onto a support, a colour path in the $a^*b^*$ plane of the CIE 1976 colorimetric space that corresponds to a variation $Dh°$ in the hue angle $h°$ of at least 20° when the angle of observation relative to the normal is varied between 0° and 80°, for an incident light angle of 45°.

The colour path may be measured, for example, using an Instrument Systems brand spectrogonioreflectometer of reference GON 360 Goniometer, after the composition has been spread in fluid form to a thickness of 300 μm using an automatic spreader onto an Erichsen brand contrast card of reference Typ 24/5, the measurement being taken on the black background of the card.

The goniochromatic pigment may be chosen, for example, from multilayer interference structures and liquid-crystal colouring agents.

In the case of a multilayer structure, it may comprise, for example, at least two layers, each layer being made, for example, from at least one material chosen from the group consisting of the following materials: $MgF_2$, $CeF_3$, ZnS, ZnSe, Si, $SiO_2$, Ge, Te, $Fe_2O_3$, Pt, Va, $Al_2O_3$, MgO, $Y_2O_3$, $S_2O_3$, SiO, $HfO_2$, $ZrO_2$, $CeO_2$, $Nb_2O_5$, $Ta_2O_5$, $TiO_2$, Ag, Al, Au, Cu, Rb, Ti, Ta, W, Zn, $MoS_2$, cryolite, and alloys, polymers and combinations thereof.

The multilayer structure may or may not have, relative to a central layer, symmetry in the chemical nature of the stacked layers.

Different effects are obtained depending on the thickness and the nature of the various layers.

Examples of symmetrical multilayer interference structures are, for example, the following structures: $Fe_2O_3/SiO_2/Fe_2O_3/SiO_2/Fe_2O_3$, a pigment having this structure being sold under the name Sicopearl by the company BASF; $MoS_2/SiO_2$/mica-oxide/$SiO_2/MoS_2$; $Fe_2O_3/SiO_2$/mica-oxide/$SiO_2/Fe_2O_3$; $TiO_2/SiO_2/TiO_2$ and $TiO_2/Al_2O_3/TiO_2$, pigments having these structures being sold under the name Xirona by the company Merck.

The liquid-crystal colouring agents comprise, for example, silicones or cellulose ethers onto which are grafted mesomorphic groups. Examples of liquid-crystal goniochromatic particles that may be used include, for example, those sold by the company Chenix and also the products sold under the name Helicone® HC by the company Wacker.

Goniochromatic pigments that may also be used include certain nacres, pigments with effects on a synthetic substrate, especially a substrate such as alumina, silica, borosilicate, iron oxide or aluminium, or interference flakes obtained from a polyterephthalate film.

Non-limiting examples of goniochromatic pigments that may be mentioned in particular, alone or as mixtures, include the goniochromatic pigments SunShine® sold by Sun, Cosmicolor Celeste® from Toyo Aluminium K.K., Xirona® from Merck and Reflecks Multidimensions® from BASF.

These particles may optionally comprise or be covered with optical brightener(s) (or white organic fluorescent substances).

Optical brighteners are compounds well known to a person skilled in the art. Such compounds are described in "Fluorescent Whitening Agent, Encyclopedia of Chemical Technology, Kirk-Othmer", vol. 11, pp. 227-241, 4th Edition, 1994, Wiley.

Their use in cosmetics in particular exploits the fact that they consist of chemical compounds having fluorescence properties, which absorb in the ultraviolet region (maximum absorption at a wavelength of less than 400 nm) and re-emit energy by fluorescence for a wavelength of between 380 nm and 830 nm. They may be defined more particularly as compounds that absorb essentially in the UVA region between 300 and 390 nm and re-emit essentially between 400 and 525 nm. Their lightening effect is based more particularly on an emission of energy between 400 and 480 nm, which corresponds to an emission in the blue part of the visible region, which contributes to lightening the skin visually when this emission takes place on the skin.

Optical brighteners that are especially known include stilbene derivatives, in particular polystyrylstilbenes and triazinylstilbenes, coumarin derivatives, in particular hydroxycoumarins and aminocoumarins, oxazole, benzoxazole, imidazole, triazole and pyrazoline derivatives, pyrene derivatives, porphyrin derivatives and mixtures thereof.

The optical brighteners that may be used may also be in the form of copolymers, for example of acrylates and/or methacrylates, grafted with optical brightener groups as described in patent application FR 99 10942.

Additional Fillers

The term "fillers" should be understood as meaning colourless or white solid particles of any form, which are in a form that is insoluble and dispersed in the medium of the composition, and are of mineral or organic nature.

In the present patent application, "mineral filler" is understood to mean any mineral solid that is insoluble in the medium at room temperature (25° C.).

The term "mineral" refers to any compound or polymer whose chemical structure does not comprise any carbon atoms.

The fillers may or may not be surface-coated, and in particular they may be surface-treated with silicones, amino acids, fluoro derivatives or any other substance that promotes the dispersion and compatibility of the filler in the composition.

Such fillers are distinct from the mineral thickeners and also from the colouring agents described previously.

The fillers may be spherical, i.e. they may comprise at least a rounded general portion, preferably defining at least a sphere portion, preferably internally defining a concavity or a hollow (sphere, globules, bowls, horseshoe, and the like), or lamellar.

Such fillers are advantageously chosen from:
  silica powders, such as the porous silica microspheres sold under the name Silica Beads SB-700 by the company Miyoshi or Sunsphere® H51 or Sunsphere® H33 by the company Asahi Glass; or the polydimethylsiloxane-coated amorphous silica microspheres sold under the name SA Sunsphere® H33 or SA Sunsphere® H-53 by the company Asahi Glass, acrylic (co)polymer powders and derivatives thereof, in particular:
the polymethyl methacrylate powder sold under the names Covabead® LH85 by the company Wackher or Microsphere M-100® by the company Matsumoto,
the polymethyl methacrylate/ethylene glycol dimethacrylate powder sold under the name Dow Corning 5640 Microsponge® Skin Oil Adsorber by the company Dow Corning or Ganzpearl® GMP-0820 by the company Ganz Chemical,
the polyallyl methacrylate/ethylene glycol dimethacrylate powder sold under the name Poly-Pore® L200 or Poly-Pore® E200 by the company Amcol Health and Beauty Solutions Inc.,
the ethylene glycol dimethacrylate/lauryl methacrylate copolymer powder sold under the name Polytrap® 6603 by the company Dow Corning,
the optionally crosslinked acrylate/alkyl acrylate copolymer crosslinked acrylate/ethylhexyl acrylate copolymer powder sold under the name Techpolymer ACP-8C by the company Sekisui Plastics,
the ethylene/acrylate copolymer powder, such as the product sold under the name Flobeads® by the company Sumitomo Seika Chemicals,
the expanded hollow particles of acrylonitrile (co)polymer sold under the name Expancel by Expancel or the microspheres sold under the name Micropearl F 80 ED® by the company Matsumoto,
the polyurethane powders sold, for example, under the names Plastic Powder D-400, Plastic Powder CS-400, Plastic Powder D-800 and Plastic Powder T-75 by the company Toshiki, silicone powders advantageously chosen from:
polymethylsilsesquioxane powders, in particular those sold under the name Tospearl, in particular Tospearl 145 A, by the company Momentive Performance Materials,
organopolysiloxane elastomer powders coated with silicone resin, especially with silsesquioxane resin, such as the products sold under the name KSP-100, KSP-101, KSP-102, KSP-103, KSP-104 or KSP-105 by the company Shin-Etsu (INCI name: vinyl dimethicone/methicone silsesquioxane crosspolymer),
silicone elastomer powders, such as the products sold under the name Trefil® Powder E-505C or Trefil® Powder E-506C by the company Dow Corning,
powders of organosilicone particles, for example, in the form of bowls, such as those described in JP-2003 128 788 or JP-A-2000-191789 or also in patent application EP 1 579 841 and sold especially by the company Takemoto Oil & Fat,
polyamide powders, such as Nylon® powders, in particular Nylon 12 powders, such as the nylon powders sold under the name Orgasol® 2002 EXS NAT COS by the company Arkema,
powders of natural organic materials, such as polysaccharide powders and in particular starch powders, especially crosslinked or non-crosslinked corn, wheat or rice starch powders, powders of starch crosslinked with octenylsuccinic anhydride sold under the name Dry-Flo® by the company National Starch or powders of waxy corn starch, such as those which are sold under the names C* Gel 04201 by the company Cargill, Corn Starch B by the company Roquette and Organic Corn Starch by the company Draco Natural Products, spherical cellulose microparticles, such as Cellulobeads D-10, Cellulobeads D-5 and Cellulobeads USF, sold by the company Daito Kasei Kogyo, particles of N—($C_8$-$C_{22}$ carbon atom acylated) amino acids; the amino acid may be, for example, lysine, glutamic acid or alanine, preferably lysine, for example Amihope LL by the company Ajinomoto or the product sold under the name Corum 5105 S by the company Corum, Perlite powders, such as those sold by the company World Minerals under the trade name Perlite P1430, Perlite P2550, Perlite P2040 or OpTiMat™ 1430 OR or 2550 OR. Europerl EMP-2 and Europerl 1 by the company Imerys, zeolites, such as the products sold by the company Zeochem under the names Zeoflair 300, Zeoflair 200, Zeoflair 100, X-Mol and X-Mol MT, calcium magnesium carbonate particles, such as those sold by the company Imerys under the name Calcidol, by the company LCW (Sensient) under the name Carbomat or by the company Omya under the name Omyacare S 60-AV.

Use may also be made of talc particles, for example sold under the names Luzenac Pharma M and UM by the company Imerys and Rose Talc and Talc SG-2000 by the company Nippon Talc; natural or synthetic mica particles, such as those sold under the names Mica M RP and Silk Mica by the company Merck, or the product sold under the name Sericite S-152-BC by the company Miyoshi Kasei; calcium carbonate and magnesium hydrogen carbonate; hydroxyapatite; boron nitride; fluorphlogopite; and mixtures thereof.

The spherical fillers may be coated with a hydrophobic treatment agent. The hydrophobic treatment agent may be chosen from fatty acids, for instance stearic acid; metal soaps, for instance aluminium dimyristate, the aluminium salt of hydrogenated tallow glutamate; amino acids; N-acylamino acids or salts thereof; lecithin, isopropyl triisostearyl titanate, and mixtures thereof. The N-acylamino acids may comprise an acyl group containing from 8 to 22 carbon atoms, for instance a 2-ethylhexanoyl, caproyl, lauroyl, myristoyl, palmitoyl, stearoyl or cocoyl group. The salts of these compounds may be the aluminium, magnesium, calcium, zirconium, zinc, sodium or potassium salts. The amino acid may be, for example, lysine, glutamic acid or alanine. The term "alkyl" mentioned in the compounds cited above especially denotes an alkyl group containing from 1 to 30 carbon atoms and preferably containing from 5 to 16 carbon atoms.

The composition advantageously has a content of additional filler(s) of between 0.1% and 10% by weight, relative to the weight of the composition, preferably between 0.1% and 5% by weight and even more preferably from 0.1% to 2.5% by weight relative to the weight of the composition.

Optional Additives

The composition may comprise at least one optional ingredient chosen, for example, from nonvolatile, hydrocarbon-based or silicone-based, polar or apolar oils; film-forming agents other than the stabilized polymer particles described previously; antioxidants; preserving agents; fragrances; flavourings; neutralizers; emollients; coalescers; moisturizers; vitamins, and mixtures thereof.

Needless to say, a person skilled in the art will take care to select the optional additional additives and/or the amount thereof such that the advantageous properties of the composition according to the invention are not, or are not substantially, adversely affected by the envisaged addition.

The compositions according to the invention are thus intended for caring for and/or making up keratin materials, in particular the skin or the lips, and also keratin fibres especially such as the eyelashes or the eyebrows.

They advantageously contain a physiologically acceptable medium, in other words a medium that is compatible with the treated keratin materials.

A composition according to the invention may more particularly be a composition for making up and/or caring for keratin materials, in particular the lips.

According to a preferred embodiment, a composition of the invention is in liquid form.

The invention is illustrated in more detail in the following examples.

All the percentages of reagents described in the examples are weight percentages.

EXAMPLES

Synthesis Examples

Example 1

In a first step, 1300 g of isododecane, 337 g of isobornyl acrylate, 28 g of methyl acrylate and 3.64 g of tert-butyl peroxy-2-ethylhexanoate (Trigonox 21 S from Akzo) were placed in a reactor. The isobornyl acrylate/methyl acrylate mass ratio is 92/8. The mixture was heated at 90° C. under argon with stirring.

After 2 hours of reaction, 1430 g of isododecane were added to the reactor feedstock and the mixture was heated to 90° C.

In a second step, a mixture of 1376 g of methyl acrylate, 1376 g of isododecane and 13.75 g of Trigonox 21 S were run in over 2 hours 30 minutes, and the mixture was left to react for 7 hours. 3.3 liters of isododecane were then added and part of the isododecane was evaporated off to obtain a solids content of 50% by weight.

A dispersion of methyl acrylate particles stabilized with a statistical copolymer stabilizer containing 92% isobornyl acrylate and 8% methyl acrylate in isododecane was obtained.

The oily dispersion contains in total (stabilizer+particles) 80% methyl acrylate and 20% isobornyl acrylate.

The polymer particles of the dispersion have a number-average size of about 160 nm.

The dispersion is stable after storage for 7 days at room temperature (25° C.).

Example 2

A dispersion of polymer in isododecane was prepared according to the preparation method of Example 1, using:

Step 1: 275.5 g of isobornyl acrylate, 11.6 g of methyl acrylate, 11.6 g of ethyl acrylate, 2.99 g of Trigonox 21, 750 g of isododecane; followed by addition, after reaction, of 750 g of isododecane.

Step 2: 539.5 g of methyl acrylate, 539.5 g of ethyl acrylate, 10.8 g of Trigonox 21S, 1079 g of isododecane. After reaction, addition of 2 liters of isododecane and evaporation to obtain a solids content of 35% by weight.

A dispersion in isododecane of methyl acrylate/ethyl acrylate (50/50) copolymer particles stabilized with an isobornyl acrylate/methyl acrylate/ethyl acrylate (92/4/4) statistical copolymer stabilizer was obtained.

The oily dispersion contains in total (stabilizer+particles) 40% methyl acrylate, 40% ethyl acrylate and 20% isobornyl acrylate.

The dispersion is stable after storage for 7 days at room temperature (25° C.).

Example 3

A dispersion of polymer in isododecane was prepared according to the preparation method of Example 1, using:

Step 1: 315.2 g of isobornyl acrylate, 12.5 g of methyl acrylate, 12.5 g of ethyl acrylate, 3.4 g of Trigonox 21, 540 g of isododecane, 360 g of ethyl acetate; followed by addition, after reaction, of 540 g of isododecane and 360 g of ethyl acetate.

Step 2: 303 g of methyl acrylate, 776 g of ethyl acrylate, 157 g of acrylic acid, 11 g of Trigonox 21S, 741.6 g of isododecane and 494.4 g of ethyl acetate. After reaction, addition of 3 liters of an isododecane/ethyl acetate mixture (60/40 weight/weight) and total evaporation of the ethyl acetate and partial evaporation of the isododecane to obtain a solids content of 44% by weight.

A dispersion in isododecane of methyl acrylate/ethyl acrylate/acrylic acid (24.5/62.8/12.7) copolymer particles stabilized with an isobornyl acrylate/methyl acrylate/ethyl acrylate (92/4/4) statistical copolymer stabilizer was obtained.

The oily dispersion contains in total (stabilizer+particles) 10% acrylic acid, 20% methyl acrylate, 50% ethyl acrylate and 20% isobornyl acrylate.

The dispersion is stable after storage for 7 days at room temperature (25° C.).

Example 4

A dispersion of polymer in isododecane was prepared according to the preparation method of Example 1, using:

Step 1: 315.2 g of isobornyl acrylate, 12.5 g of methyl acrylate, 12.5 g of ethyl acrylate, 3.4 g of Trigonox 21, 540 g of isododecane, 360 g of ethyl acetate; followed by addition, after reaction, of 540 g of isododecane and 360 g of ethyl acetate.

Step 2: 145 g of methyl acrylate, 934 g of ethyl acrylate, 157 g of acrylic acid, 12.36 g of Trigonox 21 S, 741.6 g of isododecane and 494.4 g of ethyl acetate. After reaction, addition of 3 liters of an isododecane/ethyl acetate mixture (60/40 weight/weight) and total evaporation of the ethyl acetate and partial evaporation of the isododecane to obtain a solids content of 44% by weight.

A dispersion in isododecane of methyl acrylate/ethyl acrylate/acrylic acid (11.7/75.6/12.7) copolymer particles stabilized with an isobornyl acrylate/methyl acrylate/ethyl acrylate (92/4/4) statistical copolymer stabilizer was obtained.

The oily dispersion contains in total (stabilizer+particles) 10% acrylic acid, 10% methyl acrylate, 60% ethyl acrylate and 20% isobornyl acrylate.

The dispersion is stable after storage for 7 days at room temperature (25° C.).

Example 5

A dispersion of polymer in isododecane was prepared according to the preparation method of Example 1, using:

Step 1: 48 g of isobornyl acrylate, 2 g of methyl acrylate, 2 g of ethyl acrylate, 0.52 g of Trigonox 21, 57.6 g of isododecane, 38.4 g of ethyl acetate; followed by addition, after reaction, of 540 g of isododecane and 360 g of ethyl acetate.

Step 2: 98 g of methyl acrylate, 73 g of ethyl acrylate, 25 g of maleic anhydride, 1.96 g of Trigonox 21S, 50.4 g of isododecane and 33.60 g of ethyl acetate. After reaction, addition of 1 liter of an isododecane/ethyl acetate mixture (60/40 weight/weight) and total evaporation of the ethyl acetate and partial evaporation of the isododecane to obtain a solids content of 46.2% by weight.

A dispersion in isododecane of methyl acrylate/ethyl acrylate/maleic anhydride (50/37.2/12.8) copolymer particles stabilized with an isobornyl acrylate/methyl acrylate/ethyl acrylate (92/4/4) statistical copolymer stabilizer was obtained.

The oily dispersion contains in total (stabilizer+particles) 10% maleic anhydride, 30% methyl acrylate, 40% ethyl acrylate and 20% isobornyl acrylate.

The dispersion is stable after storage for 7 days at room temperature (25° C.).

Example 6

A dispersion of polymer in isododecane was prepared according to the preparation method of Example 1, using:

Step 1: 48.5 g of isobornyl methacrylate, 4 g of methyl acrylate, 0.52 g of Trigonox 21, 115 g of isododecane; followed by addition, after reaction, of 80 g of isododecane.

Step 2: 190 g of methyl acrylate, 1.9 g of Trigonox 21S, 190 g of isododecane. After reaction, addition of 1 liter of isododecane and partial evaporation of the isododecane to obtain a solids content of 48% by weight.

A dispersion in isododecane of methyl acrylate polymer particles stabilized with an isobornyl methacrylate/methyl acrylate (92/8) statistical copolymer stabilizer was obtained.

The oily dispersion contains in total (stabilizer+particles) 80% methyl acrylate and 20% isobornyl methacrylate.

The dispersion is stable after storage for 7 days at room temperature (25° C.).

Examples 7 and 8 (Invention) and 9 and 10 (Outside the Invention)

Several oily dispersions of polymethyl acrylate stabilized with a stabilizer containing isobornyl acrylate and optionally methyl acrylate were prepared, according to the procedure of Example 1, by varying the mass ratio of isobornyl acrylate and methyl acrylate and observing the stability of the dispersion obtained as a function of the chemical constitution of the stabilizer.

All the dispersions comprise in total (stabilizer+particles) 80% methyl acrylate and 20% isobornyl acrylate.

Example 7

Step 1: 50 g of isobornyl acrylate, 0.5 g Trigonox 21, 96 g of isododecane; followed by addition, after reaction, of 80 g of isododecane.

Step 2: 200 g of methyl acrylate, 2 g of Trigonox 21S, 200 g of isododecane. After reaction, addition of 80 g of isododecane and evaporation to obtain a solids content of 31% by weight.

A dispersion in isododecane of polymethyl acrylate particles stabilized with a polyisobornyl acrylate stabilizer was obtained.

Example 8

Step 1: 48.5 g of isobornyl acrylate, 8.5 g of methyl acrylate, 0.57 g Trigonox 21, 115 g of isododecane; followed by addition, after reaction, of 75 g of isododecane.

Step 2: 185.5 g of methyl acrylate, 1.85 g of Trigonox 21S, 185.5 g of isododecane. After reaction, addition of 75 g of isododecane and evaporation to obtain a solids content of 31% by weight.

A dispersion in isododecane of polymethyl acrylate particles stabilized with an isobornyl acrylate/methyl acrylate (85/15) statistical copolymer stabilizer was obtained.

Example 9 (Outside the Invention)

Step 1: 48.5 g of isobornyl acrylate, 12 g of methyl acrylate, 0.6 g Trigonox 21, 115 g of isododecane; followed by addition, after reaction, of 60 g of isododecane.

Step 2: 182 g of methyl acrylate, 1.82 g of Trigonox 21S, 182 g of isododecane. After reaction, addition of 60 g of isododecane and evaporation to obtain a solids content of 31% by weight.

A dispersion in isododecane of polymethyl acrylate particles stabilized with an isobornyl acrylate/methyl acrylate (80/20) statistical copolymer stabilizer was obtained.

Example 10 (Outside the Invention)

Step 1: 48.5 g of isobornyl acrylate, 21 g of methyl acrylate, 0.7 g Trigonox 21, 130 g of isododecane; followed by addition, after reaction, of 65 g of isododecane.

Step 2: 173 g of methyl acrylate, 1.73 g of Trigonox 21S, 173 g of isododecane. After reaction, addition of 65 g of isododecane and evaporation to obtain a solids content of 31% by weight.

A dispersion in isododecane of polymethyl acrylate particles stabilized with an isobornyl acrylate/methyl acrylate (70/30) statistical copolymer stabilizer was obtained.

The stability 12 hours after the end of synthesis of the oily dispersions of polymethyl acrylate of Examples 1 and 7 to 10 was compared, and the following results were obtained.

| Example | Stabilizer | Stability |
|---|---|---|
| 1 | 92 isobornyl acrylate/ 8 methyl acrylate | Stable |
| 7 | 100 isobornyl acrylate | Stable |
| 8 | 85 isobornyl acrylate/ 15 methyl acrylate | Stable |
| 9 | 80 isobornyl acrylate/ 20 methyl acrylate | Phase separation and setting to a solid |
| 10 | 70 isobornyl acrylate/ 30 methyl acrylate | Phase separation and setting to a solid |

The results obtained show that the dispersions of polymethyl acrylate in isododecane are stable when the stabilizer is an isobornyl acrylate homopolymer or an isobornyl acrylate/methyl acrylate copolymer with an isobornyl acrylate/methyl acrylate weight ratio>80/20.

Moreover, the film obtained with the oily dispersions of Examples 1, 7 and 8 have the following properties:

| Gloss at 20° | Resistance to fatty substances | Tacky |
|---|---|---|
| 72 | Resistant to fatty substances | Non-tacky |
| 69 | Resistant to fatty substances | Non-tacky |
| 65 | Resistant to fatty substances | Non-tacky |

Examples 11 and 12 (Outside the Invention)

Tests were performed with other monomers bearing a cyclic group by replacing the isobornyl acrylate, performing step 1 of Example 1, i.e. preparing a cyclic monomer/methyl acrylate (92/8) statistical copolymer stabilizer. All the stabilizers prepared in isododecane led to a medium that set to a solid in the form of a viscous precipitate. This shows that such stabilizers are unsuitable for forming an oily dispersion since they are incompatible with isododecane, in contrast with the stabilizers prepared in Examples 1 to 8 described previously.

| Examples | Stabilizer | Compatibility in isododecane |
|---|---|---|
| 11 | Cyclohexyl acrylate/ methyl acrylate (92/8) | Incompatible (viscous precipitate) |
| 12 | Cyclohexyl methacrylate/ methyl acrylate (92/8) | Incompatible (viscous precipitate) |

Example 13

Liquid Lipsticks

The following compositions, the ingredients of which are collated in the table below, are prepared.

The percentages are given as weight relative to starting materials, unless otherwise indicated.

| Ingredients | Composition 1 invention | Composition 2 comparative |
|---|---|---|
| Tributyl citrate | 3.73 | 3.73 |
| Disteardimonium hectorite (Bentone Gel ISDV; Elementis, (hectorite, isododecane, propylene glycol) | 10 | 10 |
| Ethylcellulose (Aquacoat ® ECD 30 from FMC Biopolymer; dispersion in water of ethylcellulose; sodium lauryl sulfate and cetyl alcohol; 30% solids) | 26.3 | — |
| Water | — | 26.3 |
| (Methyl acrylate)-co-(ethyl acrylate)-co-(acrylic acid)-co-(isobornyl acrylate) copolymer in isododecane according to Example 4 | 52.35 | 52.35 |
| Cetyl PEG/PPG-10/1 Dimethicone (ABIL EM 90 from Evonik Industries) | 1.5 | 1.5 |
| C30-45 Alkyldimethylsilyl polypropylsilsesquioxane (Dow Corning SW-8005 C30 Resin Wax from Dow Corning) | 0.53 | 0.53 |
| Triglyceryl-4 Isostearate (Isolan GI 34 from Evonik Industries) | 0.5 | 0.5 |
| Pigments | 3.33 | 3.33 |
| Preserving agent | 0.7 | 0.7 |
| Isododecane | qs | qs |

Preparation Protocol

The dispersion of ethylcellulose and the preserving agent is mixed at room temperature in a beaker with stirring using a magnetic bar.

Separately, the dispersion of polymer particles according to Example 4 is mixed with the Bentone gel, the silicone wax predissolved under hot conditions in part of the isododecane, and the remaining isododecane in a suitable container with a speed mixer until a smooth, homogeneous mixture is obtained.

The surfactants (Isolan GI 34 and Abil EM 90) are then introduced into the preceding mixture in a heating pan and the whole is homogenized using a mixer for 2 minutes until a homogeneous, soft, white and opaque phase is obtained.

The pigments preground in part of the isododecane and the tributyl citrate are then added and the whole is homogenized.

The aqueous phase comprising the ethylcellulose is then introduced to obtain the emulsion, and the whole is mixed (mixer, for about 3 minutes) until a thick, smooth, glossy and homogeneous mixture is obtained.

Evaluation of the Compositions

Oil Resistance Test:

The composition is applied to an artificial keratin material support (25 μm wet film thickness).

The sample is left to dry for 24 hours at 35° C.

After the drying step, one drop of olive oil is placed on the film of composition and left for 10 minutes.

The oil is then wiped five times using cotton wool.

The integrity of the film after wiping with cotton wool is evaluated to evaluate the oil resistance of the composition, on a scale ranging from 1 to 3 (1: excellent resistance, 2: intermediate resistance, and 3: poor resistance).

Tack Evaluation Protocol:

The composition is applied to the lips so as to form a deposit of homogeneous thickness.

The tacky nature on touching with a finger was evaluated during the drying of the formulation after 5 minutes at room temperature (25° C.).

To do this, a finger was applied, after the specified drying period, onto the applied formulation and the tack was assessed by the individual on removal of his finger from the applied formulation.

The two compositions are easy to apply as a deposit which, after drying, is not desiccating.

It is found that the composition according to the invention significantly improves the oil resistance and the tacky nature of the deposit, when compared with the properties of the deposit of the comparative composition.

Example 14

Liquid Lipsticks

The following compositions are prepared, the ingredients of which are collated in the table below.

The percentages are given on a weight basis relative to the starting materials, unless otherwise indicated.

| Ingredients | Composition 2 invention | Composition 3 invention |
|---|---|---|
| Tributyl citrate | | 2.5 |
| Disteardimonium hectorite (Bentone gel ISDV; Elementis) (hectorite, isododecane, propylene glycol) | 13.27 | 8 |
| Ethylcellulose (Aquacoat ® ECD 30 from FMC Biopolymer; dispersion in water of ethylcellulose; sodium lauryl sulfate, cetyl alcohol; 30% solids) | 17.17 | 18 |
| Water | — | 6.94 |
| (Methyl acrylate)-co-(ethyl acrylate)-co-(acrylic acid)-co-(isobornyl acrylate) copolymer in isododecane (according to Example 3) | 61.94 | — |
| (Methyl acrylate)-co-(ethyl acrylate)-co-(acrylic acid)-co-(isobornyl acrylate) copolymer in isododecane (according to Example 4) | — | 57 |
| C30-45 Alkyldimethylsilyl polypropylsilsesquioxane (Dow Corning SW-8005 C30 Resin Wax from Dow Corning) | 0.53 | 0.48 |
| Triglyceryl-4 isostearate (Isolan GI 34 from Evonik Industries) | 0.5 | 0.67 |
| Cetyl PEG/PPG-10/1 Dimethicone (Abil EM 90 from Evonik Industries) | 1.5 | 2 |
| Pigments | 3.33 | 2.36 |
| Preserving agent | 0.7 | 0.7 |
| Fragrance | — | 0.2 |
| Sweetener | — | 0.03 |
| Isododecane | qs | qs |

Preparation Protocol

The dispersion of ethylcellulose, the preserving agent and the sweetener are mixed in a beaker with stirring using a magnetic bar, at room temperature.

Separately, the dispersion of polymer particles according to Example 3 is mixed with the Bentone gel, the silicone wax predissolved with heating in part of the isododecane, the rest of the isododecane and the fragrance, if present, in a suitable container with a speed mixer until a smooth, homogeneous mixture is obtained.

Next, the surfactants (Isolan GI 34 and Abil EM 90) are introduced into the preceding mixture in a heating pan and the whole is homogenized using a mixer for 2 minutes until a homogeneous, smooth, white and opaque phase is obtained.

The pigments preground in part of the isododecane and the tributyl citrate are then added and the whole is homogenized.

The aqueous phase comprising the ethylcellulose is then introduced to obtain the emulsion, and the whole is mixed (mixer, for about 3 minutes) until a thick, smooth, glossy and homogeneous mixture is obtained.

Results

The compositions are easy to apply, and give a homogeneous, non-desiccating, non-tacky, oil-resistant deposit (tests performed according to the protocols detailed in the preceding example).

| | Composition 2 invention | Composition 3 invention |
|---|---|---|
| Oil resistance | Good | Good |
| Tack after 5 minutes | Good | Good |

Example 15

Liquid Lipsticks

The following compositions are prepared, the ingredients of which are collated in the table below.

The percentages are given on a weight basis relative to the starting materials, unless otherwise indicated.

|  | Composition 4 | Composition 5 |
|---|---|---|
| (Methyl acrylate)-co-(ethyl acrylate)-co-(acrylic acid)-co-(isobornyl acrylate) copolymer in isododecane (according to Example 4) | 45 | 45 |
| Tributyl citrate | 2.5 | — |
| Ethylcellulose (Aquacoat ® ECD 30 from FMC Biopolymer; dispersion in water of ethylcellulose; sodium lauryl sulfate, cetyl alcohol; 30% solids) | 15 | 15 |
| Preserving agent | 0.7 | 0.7 |
| Water | 11.69 | 11.69 |
| Hydrogenated styrene/butadiene copolymer (Kraton ® G-1657 Polymer from Kraton Polymers) | 7.8 | 3.9 |
| C30-45 Alkyldimethylsilyl polypropylsilsesquioxane (Dow Corning SW-8005 C30 Resin Wax from Dow Corning) | 0.6 | 0.6 |
| Cetyl PEG/PPG-10/1 Dimethicone (Abil EM 90 from Evonik Industries) | 2 | 2 |
| Triglyceryl-4 isostearate (Isolan GI 34 from Evonik Industries) | 0.67 | 0.67 |
| Pigments | 1 | 1 |
| Isododecane | qs | qs |

Preparation Protocol:

The dispersion of ethylcellulose and the preserving agent is mixed in a beaker with stirring using a magnetic bar at room temperature.

Separately, the dispersion of polymer particles according to Example 3 is mixed with the Bentone gel, the silicone wax predissolved under hot conditions in part of the isododecane, the Kraton predissolved in part of the isododecane, and the remaining isododecane in a suitable container with a speed mixer until a smooth, homogeneous mixture is obtained.

The surfactants (Isolan GI 34 and Abil EM 90) are then placed in the preceding mixture in a heating pan and homogenized using a mixer for 2 minutes until a white, opaque, supple, homogeneous phase is obtained.

The pigments preground in part of the isododecane and the tributyl citrate, if present, are then added and the whole is homogenized.

The aqueous phase comprising the ethylcellulose is then added to obtain the emulsion, and the whole is mixed (mixer, for about 3 minutes) until a thick, smooth, glossy and homogeneous mixture is obtained.

Results:

The compositions are easy to apply, give a uniform deposit which is non-desiccating, non-tacky and oil resistant.

The invention claimed is:

1. Composition comprising particles of at least one polymer that is surface-stabilized with a stabilizer, the polymer of the particles being a $C_1$-$C_4$ alkyl (meth)acrylate polymer, the stabilizer being an isobornyl (meth)acrylate polymer chosen from isobornyl (meth)acrylate homopolymer and statistical copolymers of isobornyl (meth)acrylate and of $C_1$-$C_4$ alkyl (meth)acrylate present in an isobornyl (meth)acrylate/$C_1$-$C_4$ alkyl (meth)acrylate weight ratio of greater than 4; at least one hydrocarbon-based oil, at least alkyl cellulose, the alkyl residue of which comprises between 2 and 6 carbon atoms; and water.

2. Composition according to claim 1, wherein the polymer of the particles is a methyl acrylate and/or ethyl acrylate polymer.

3. Composition according to claim 1, wherein the polymer of the particles comprises an ethylenically unsaturated acid monomer or an anhydride thereof.

4. Composition according to claim 1, wherein the polymer of the particles comprises from 80% to 100% by weight of $C_1$-$C_4$ alkyl (meth)acrylate and from 0 to 20% by weight of ethylenically unsaturated acid monomer, relative to the total weight of the polymer.

5. Composition according to claim 1, wherein the polymer of the particles is selected from the group consisting of:
   methyl acrylate homopolymers;
   ethyl acrylate homopolymers;
   methyl acrylate/ethyl acrylate copolymers;
   methyl acrylate/ethyl acrylate/acrylic acid copolymers;
   methyl acrylate/ethyl acrylate/maleic anhydride copolymers;
   methyl acrylate/acrylic acid copolymers,
   ethyl acrylate/acrylic acid copolymers;
   methyl acrylate/maleic anhydride copolymers, and
   ethyl acrylate/maleic anhydride copolymers.

6. Composition according to claim 1, wherein the stabilizer is a statistical copolymer of isobornyl (meth)acrylate and of $C_1$-$C_4$ alkyl (meth)acrylate present in an isobornyl (meth)acrylate/$C_1$-$C_4$ alkyl (meth)acrylate weight ratio of greater than or equal to 5.

7. Composition according to claim 1, wherein the stabilizer is selected from the group consisting of:
   isobornyl acrylate homopolymers;
   statistical copolymers of isobornyl acrylate/methyl acrylate;
   statistical copolymers of isobornyl acrylate/methyl acrylate/ethyl acrylate; and
   statistical copolymers of isobornyl methacrylate/methyl acrylate.

8. Composition according to claim 1, wherein the hydrocarbon-based oil is chosen from apolar hydrocarbon-based oils containing from 8 to 16 carbon atoms.

9. Composition according to claim 1, wherein the content of hydrocarbon-based oil ranges from 20% to 75% by weight relative to the weight of the composition.

10. Composition according to claim 1, wherein the polymer particles surface-stabilized with a stabilizer are incorporated into the composition in the form of a dispersion in at least one hydrocarbon-based oil.

11. Composition according to claim 1, wherein the content of polymer particles is from 5% to 55% by weight relative to the weight of the composition.

12. Composition according to claim 1, wherein the composition comprises at least one mineral thickener selected from the group consisting of optionally hydrophobic-modified clays, optionally hydrophobic-modified silicones, modified hectorites, bentonites, disteardimonium hectorite, stearalkonium hectorite, quaternium-18 bentonite, stearalkonium bentonite, quaternium-18/benzalkonium bentonite; optionally hydrophobic-treated fumed silicas; hydrophobic silica aerogels, and mixtures thereof.

13. Composition according to claim 1, wherein the content of mineral thickener is from 0.2% to 15% by weight relative to the weight of the composition, expressed as active material.

14. Composition according to claim 1, wherein the composition further comprises a hydrocarbon-based block copolymer comprising at least one styrene block and at least one block comprising units selected from the group consisting of butadiene, ethylene, propylene, butylene, isoprene, and mixtures thereof.

15. Composition according to claim 14, wherein the hydrocarbon-based block copolymer is selected from the group consisting of optionally hydrogenated diblock copolymers of styrene-ethylene/propylene, optionally hydrogenated diblock copolymers of styrene-ethylene/butadiene, optionally hydrogenated diblock copolymers of styrene-ethylene/butylene, styrene-isoprene copolymers, optionally hydrogenated triblock copolymers of styrene-ethylene/butadiene-styrene, optionally hydrogenated triblock copolymers of styrene-butylene/ethylene-styrene, optionally hydrogenated triblock copolymers of styrene-isoprene-styrene, optionally hydrogenated triblock copolymers of styrene-butadiene-styrene, and mixtures thereof.

16. Composition according to claim 14, wherein the content of hydrocarbon-based block copolymer is from 2.5% to 15% by weight, relative to the total weight of the composition.

17. Composition according to claim 1, wherein the water content ranges between 10% and 50% by weight relative to the weight of the composition.

18. Composition according to claim 1, wherein the alkylcellulose is chosen from ethylcellulose and propylcellulose.

19. Composition according to claim 1, wherein the alkylcellulose content is from 1% to 8% by weight relative to the weight of the composition.

20. Composition according to claim 19, wherein the composition further comprises at least one surfactant.

21. Composition according to claim 20, wherein the content of surfactant(s) in the composition ranges from 0.2% to 10% by weight, relative to the weight of the composition.

22. Process for making up and/or caring for a human keratin material in which the composition according to claim 1 is applied to the keratin material.

23. Composition according to claim 5, wherein the stabilizer is selected from the group consisting of:
   isobornyl acrylate homopolymers;
   statistical copolymers of isobornyl acrylate/methyl acrylate;
   statistical copolymers of isobornyl acrylate/methyl acrylate/ethyl acrylate; and
   statistical copolymers of isobornyl methacrylate/methyl acrylate.

24. Process for making up and/or caring for human skin in which the composition according to claim 1 is applied to the skin.

* * * * *